(12) United States Patent
Murphy et al.

(10) Patent No.: US 7,361,465 B2
(45) Date of Patent: Apr. 22, 2008

(54) METHODS AND COMPOSITIONS FOR TAILING AND AMPLIFYING RNA

(75) Inventors: George L. Murphy, Austin, TX (US); J. Penn Whitley, Austin, TX (US)

(73) Assignee: Applera Corporation, Foster City, CA (US)

( * ) Notice: Subject to any disclaimer, the term of this patent is extended or adjusted under 35 U.S.C. 154(b) by 0 days.

(21) Appl. No.: 10/935,534

(22) Filed: Sep. 7, 2004

(65) Prior Publication Data

US 2006/0051771 A1    Mar. 9, 2006

(51) Int. Cl.
C12Q 1/68      (2006.01)
C12P 19/34     (2006.01)

(52) U.S. Cl. .......................................... 435/6; 435/91.1

(58) Field of Classification Search .................. None
See application file for complete search history.

(56) References Cited

U.S. PATENT DOCUMENTS

| | | | |
|---|---|---|---|
| 5,545,522 A | 8/1996 | Van Gelder et al. | 435/6 |
| 5,716,785 A | 2/1998 | Van Gelder et al. | 435/6 |
| 5,891,636 A | 4/1999 | Van Gelder et al. | 435/6 |
| 5,932,451 A * | 8/1999 | Wang et al. | 435/91.21 |
| 6,103,474 A * | 8/2000 | Dellinger et al. | 435/6 |

FOREIGN PATENT DOCUMENTS

| | | |
|---|---|---|
| WO | WO 0043540 A1 * | 7/2000 |
| WO | WO 01/25418 | 4/2001 |
| WO | WO 2005/064019 | 7/2005 |

OTHER PUBLICATIONS

Cashdollar et al. ("Cloning the double-stranded RNA genes of reovirus: sequence of the cloned S2 gene" Proc Natl Acad Sci U S A. Dec. 1982;79(27):7644-8).*
Wahle ("Poly(A) tail length control is caused by termination of processive synthesis" J Biol Chem. Feb 10, 1995;270(6):2800-8).*
Beckel-Mitchener et al. "Poly(A) tail length-dependent stabilization of GAP-43 mRNA by the RNA-binding protein HuD" J Biol Chem. Aug. 2, 2002;277(31):27996-8002. Epub May 28, 2002).*
Whitley et al. "Enrichment of bacterial RNA for gene expression analysis from mixed host-microbe cell populations." Abstracts of the General Meeting of the American Society of Microbiology. (2003) vol. 103, pp. I-085 (see printout).*
Fuchs et al. (Ribonucleolytic activities in the *Escherichia coli* in vitro translation system and in its separate components. FEBS Lett. Sep. 8, 1997;414(2):362-4).*
Roche—http://www.roche-applied-science.com/PROD_INF/MANUALS/InSitu/pdf/ISH_33-37.pdf.*
Wendisch et al. ("Isolation of *Escherichia coli* mRNA and comparison of expression using mRNA and total RNA on DNA microarrays" Anal Biochem. Mar. 2001;290(2):205-13).*
Lingner et al. ("Purification and characterization of poly(A) polymerase from *Saccharomyces cerevisiae*" J Biol Chem. May 15, 1991;266(14):8741-6).*
Roche—http://www.roche-applied-science.com/PROD_INF/MANUALS/InSitu/pdf/ISH_33-37.pdf, May 9, 2003.*
"Bacterial RNA isolation from infected eukaryotic hosts," AMBION, The RNA Company, Nov. 2002.
Amara and Vijaya, "Specific polyadenylation and purification of total messenger RNA from *Escherichia coli*," Nulcleic Acids Research, 25(17):3465-3470, 1997.
Arfin et al., "Global gene expression profiling in *Escherichia coli* K12," *J. Biol. Chem.*, 275:29672-29684, 2000.
Eriksson et al., "Unraveling the biology of macrophage infection of gene expression profiling of intracellular *Salmonella enterica*," *Mol. Microbiol*, 47(1):103-118, 2003.
Feng et al., "Unpaired terminal nucleotides and 5' monophosphorylation govern 3' polyadenylation by *Escherichia coli* poly(A) polymerase I," *Proc. Natl. Acad. Sci., USA*, 97:6415-6420, 2000.
Grifantini et al., "Previously unrecognized vaccine candidates against group B meningococcus identified by DNA microarrays," *Nat Botechnol*, 20:914-921, 2002.
Khil and Camerini-Otero, "Over 1000 genes are involved in the DNA damage response of *Escherichia coli*," *Mol Microbiol*, 44(1):89-105, 2002.
Martin and Keller, "Tailing and 3' -end labeling of RNA with yeast poly(A) polymerase and various nucleotides," *RNA*, 4:226-230, 1998.
Motley et al., "Simultaneous analysis of host and pathogen interactions during an in vivo infection reveals local induction of host acute phase response proteins, a novel bacterial stress response, and evidence of a host-imposed metal ion limited environment," *Cellular Microbiology*, 6(9):849-865, 2004.
Staudinger et al., "mRNA expression profiles for *Escherichia coli* ingested by normal and phagocyte oxidase-deficient human neutrophils," *J. Clin Invest*, 110(8):1151-1153, 2002.
Wendisch et al., "Isolation of *Escherichia coli* mRNA and comparison of expression using mRNA and total RNA on DNA microarrays," *Anal Biochem*, 290(2):205-213, 2001.

(Continued)

Primary Examiner—Kenneth R. Horlick
Assistant Examiner—Christopher M. Babic
(74) Attorney, Agent, or Firm—Gloria L. Norberg

(57) ABSTRACT

The present invention provides methods and compositions that enable tagging and amplification of targeted RNA molecules. A targeted RNA molecule is any non-polyadenylated RNA molecule including, for example, miRNA, siRNA, rRNA, tRNA, synthetic RNA, or non-polyadenylated mRNA such as mRNA from bacteria. In certain aspects, the invention provides methods and compositions for the genome-wide expression analysis of bacterial genes. Significantly, the methods enable genome-wide expression analysis in circumstances where bacterial numbers were previously too low to purify adequate amounts of RNA for DNA microarray analysis or other applications. Such methods are particularly useful for the study of bacterial gene expression during host-cell infection. The invention also provides kits for tagging and amplifying targeted RNA molecules.

24 Claims, 2 Drawing Sheets

OTHER PUBLICATIONS

Gorziglia et al, "Molecular cloning of a human rotavirus genome," *Journal of General Virology*, 64:2585-2596, 1983.

Gunther Sillero et al., "Polyphosphates strongly inhibit the tRNA dependent synthesis of poly(A) catalyzed by poly(A) polymerase from *Saccharomyces cerevisiae*," *Febs Letters, Elsevier*, Amsterdam, NL, 550:41-45, 2003.

Hajnsdorf et al., "Host factor Hfq of *Escherichia coli* stimulates elongation of poly(A) tails by poly(A) polymerase I," *Proceedings of the National Academy of Sciences of The United States of America*, 97:1501-1505, 2000.

Rosenow et al., "Prokaryotic RNA preparation methods useful for high density array analysis: comparison of two approaches," *Nucleic Acids Research*, 29:E112-(1-8), 2001.

Wang et al., "A regulatory cytoplasmic poly(A) polymerase in *Caenorhabditis elegans*," *Nature* (London), 419:312-316, 2002.

Whitley et al., "Enrichment of bacterial RNA for gene expression analysis from mixed host-microbe cell populations," *Abstracts of the General Meeting of the American Society for Microbiology*, 103:I-085, 2003.

Yehudai-Resheff et al., "Characterization of the *E.coli* poly(A) polymerase: nucleotide specificity, RNA-binding affinities and RNA structure dependence," *Nulcleic Acids Research*, 28:1139-1144, 2000.

Aviv and Leder, "Purification of Biologically Active Globin Messenger RNA by Chromatography on Oligothymidylic acid-Cellulose," *Proc. Natl. Acad. Sci*, USA, 69(6) :1408-1412, 1972.

Cao and Sarkar, "Stationary Phase-Specific mRNAs in *Escherichia coli* Are Polyadenylated," *Biochem. Biophys. Res. Commun.*, 239(1): 46-50, 1997.

Engel and Davidson, "Addition of Poly(adenylic acid) to RNA Using Polynucleotide Phosphorylase: An Improved Method for Electron Microscopic Visualization of RNA-DNA Hybrids," *Biochemistry*, 17(18) :3883-3888, 1978.

Eun, "DNA-Independent RNA Polymerase: Poly(A) Polymerase," In: *Enzymology Primer for Recombinant DNA Technology*, Academic Press, NY, 555-565, 1996.

Linger et al., "Purification and Characterization of Poly(A) Polymerase from *Saccharomyces cervisiae*," The Journal of Biological Chemistry, vol. 266, No. 14:8741-8746, May 15, 1991.

Lockhart et al., "Expression Monitoring by Hybridization to High-Density Olignucleotides Arrays," *Nat. Biotechnol.*, 14(13) :1675-1680, 1996.

Mohanty and Kushner, "Residual polyadenylation in poly(A) polymerase I (pcnB) mutants of *Escherichia coli* does not result from the activity encoded by the *f310* gene," *Mol. Microbiol.*, 34(5): 1109-1119, 1999.

Mohanty and Krushner, "Polynucleotide phosphorylase, RNase II and RNase E play different roles in the in vivo modulation of polyadenylation in *Escherichia coli*," *Mol. Microbiol.*, 36(4) :982-94, 2000.

Raynal et al., "Bacterial poly (A) polymerase: An enzyme that modulates RNA stability," *Biochimie*, 78, 390-398, 1996.

Read and Norbury, "Roles for Cytoplasmic Poladenylation in Cell Cycle Regulation," *J. Cell Biochem*, 87(3) :258-265, 2002.

Written Opinion and Search Report mailed May 30, 2006 for PCT/US05/032227 filed Sep. 7, 2005 entitled "Methods and Compositions for Tailing and Amplifying RNA," Inventors: George L. Murphy and J. Penn Whitley; Applicant: Ambion Inc.

* cited by examiner

METHODS AND COMPOSITIONS FOR TAILING AND AMPLIFYING RNA

BACKGROUND OF THE INVENTION

1. Field of the Invention

The present invention relates generally to the field of molecular biology. More particularly, it concerns methods and compositions for tailing and amplifying non-polyadenylated RNA molecules, including microRNA, siRNA, tRNA, rRNA, synthetic RNA, and non-polyadenylated mRNA, such as mRNA from bacteria or fragments of prokaryotic or eukaryotic mRNAs such as may be encountered in degraded RNA samples.

2. Description of Related Art

The commonly used method for mRNA purification from eukaryotic cells, oligo-dT capture, is ineffective for capturing RNA molecules lacking poly(A) tails. Examples of RNA molecules that are not polyadenylated include microRNA, siRNA, tRNA, rRNA, synthetic RNA, and non-polyadenylated mRNA from prokaryotes. In addition, mRNA fragments, such as may be encountered in degraded RNA samples, may also lack poly(A) tails. The study of these important RNA molecules is hindered by inadequate methods for their isolation and amplification.

For example, small RNAs, such as microRNA (miRNA) and small interfering RNA (siRNA), have emerged as powerful post-transcriptional regulators of gene expression in many different organisms, thus making the analysis of small RNA molecules increasingly important. To generate scientifically accurate data, the analysis of small RNA molecules requires their quantitative purification and amplification. There is a need for novel methods and compositions that are capable of quantitatively purifying and amplifying these important molecules.

Another example of the difficulties encountered when analyzing non-polydenylated RNA molecules is the study of bacterial gene expression. The ability to evaluate global gene expression responses of bacterial pathogens during host cell infections is seen as crucial for identifying novel bacterial targets for therapeutic intervention and for a comprehensive understanding of bacterial pathogenesis. However, methods for in vivo whole genome expression analyses have not been fully realized. Genome-wide analysis of bacterial gene expression, following growth in the presence of host cells in vitro or in vivo, has been referred to as the "Holy Grail" of pathogen expression analysis (Sassetti and Rubin, 2002). Others have more recently reiterated that this remains the "ultimate goal" of pathogen gene expression analysis (Schoolnik, 2002; Conway and Schoolnik, 2003). The technical difficulties that hinder these studies include (1) purifying bacterial RNA free from large amounts of contaminating host cell RNA, and (2) purifying adequate amounts of bacterial RNA for DNA microarray analysis.

Bacteria respond rapidly to changes in their microenvironments. This quick adaptability enables them to survive and grow in all kinds of environmental conditions, including of course, eukaryotic host organisms. Many studies with bacterial pathogens have shown that bacteria exhibit altered gene/protein expression during interactions with host cells. In the past few years, host-induced changes in bacterial gene expression have been identified for *Neisseria meningitidis* (Taha et al., 1998; Grifantini et al., 2002; Dietrich et al., 2003), *Mycobacterium tuberculosis* (Triccas et al., 1999), *Salmonella* spp. (Eriksson et al., 2003; Valdiva and Falkow, 1997), *Brucella suis* (Boschiroli et al., 2002), and *Legionella pneumophila* (Abu Kwaik, 1998), to name a few. Analyses of bacterial gene expression during interactions with host cells will provide information on (1) the specific conditions of the host microenvironment (e.g., within phagocytic vacuoles, (Staudinger et al., 2002), (2) mechanisms and pathways used by bacteria in response to those microenvironments, (3) proteins that are essential for survival and growth in vivo, (4) novel vaccine candidates, and (5) novel targets for antibiotics.

Identifying bacterial genes whose expression is altered by host cells has not been easy, and microbiologists have used numerous techniques to address the challenge. These include mRNA-subtracted cDNA libraries (Scott-Craig et al., 1991; Plum and Clark-Curtiss, 1994), in vivo expression technology (IVET, (Mahan et al., 1993), signature tagged mutagenesis (Hensel et al., 1995), gene fusions with lacZ (Taha et al., 1998) and gfp (Triccas et al., 1999; Valdiva and Falkow, 1997; Boschiroli et al., 2002), differential display PCR (Abu Kwaik and Pederson, 1996), one- and two-dimensional electrophoresis of cell proteins (Abu Kwaik, 1998; Abshire and Neidhardt, 1993; Monahan et al., 2001), and cDNA selection (SCOTS-selective capture of transcribed sequences, (Graham and Clark-Curtiss, 1999). Many of these techniques have proven invaluable for the initial identification of specific bacterial genes whose expression is altered by interaction with host cells. However, all of these methods have limitations. Most require significant genetic manipulation (construction of mutants, libraries, gene fusions) and are labor intensive. Chief amongst the limitations is that none allows for quantification of genome-wide expression. Two-dimensional protein electrophoresis comes closest to allowing global expression analyses. However, at this point, it too is limited by resolution and sensitivity.

A handful of research studies have appeared in which investigators have overcome the technical difficulties described above. Investigators at Chiron and The Institute For Genomic Research (TIGR) used microarrays to analyze gene expression of *Neisseria meningitidis* following adherence to cultured epithelial cells (Grifantini et al., 2002). To reduce contaminating host-cell RNA, the epithelial cells were selectively lysed with saponin (a cholesterol-binding detergent), bacterial cells were harvested, and RNA was purified. Another group used SDS to selectively lyse macrophages containing phagocytized *Salmonella enterica* (Eriksson et al., 2003). RNA was then purified from the harvested bacteria. Staudinger et al. (2002) harvested total RNA from neutrophils with internalized *E. coli*. The authors reported that bacterial RNA was estimated to be ⅕ or more of the RNA isolated from the sample. Staudinger et al. used gene-specific primers for cDNA synthesis prior to *E. coli* array analysis.

Selective eukaryotic cell lysis followed by harvesting of bacteria is a useful method for increasing the relative amount of bacterial RNA isolated from microbe-host cell mixtures. It is imperative that RNA be stabilized prior to such treatments. If it is not, detergent treatment will likely alter the gene expression profile of the bacteria. In addition, selective detergent lysis of host cells is less effective with many Gram-negative bacteria that are easily lysed with such detergents (e.g., *Yersinia enterocolitica*). Furthermore, variable susceptibility of eukaryotic cells to saponin-mediated lysis makes optimization difficult. Selective eukaryotic cell lysis may be least useful with infected tissue samples that require vigorous homogenization to effect cell lysis. Nonetheless, selective lysis of host cells with detergents is a good idea that can be helpful for reducing excessive amounts of host cell RNA.

The use of gene-specific primers with bacterial arrays is another method (Staudinger et al., above) that has been used in hope of specifically priming bacterial RNA's. But, this results in the loss of ~30% of hybridization signals on *E. coli* arrays (Khil and Camerini-Otero, 2002; Arfin et al., 2000).

A small percentage of bacterial mRNAs are poly(A)-tailed, but these are targeted for degradation and tend to be unstable. As a result, the commonly used method for mRNA purification with eukaryotic cells, oligo-dT capture, is ineffective for capturing bacterial mRNAs. Methods to polyadenylate bacterial mRNAs, thereby allowing for their purification by oligo dT-capture have been developed. Amara and Vijaya (1997) demonstrated that mRNAs in purified polysomes can be specifically polyadenylated and purified by oligo-dT capture. However, using their method Amara and Vijaya were not able to efficiently poly(A) tail the transcripts. For example, they reported that only 50% of the NS3 messages were polyadenylated. Wendisch et al. (2001) showed that the same process can be carried out with crude cell extracts.

As suggested above, several shortcomings are associated with the polyadenylation approach described in the prior art. Different mRNAs may be polyadenylated to different extents or not at all depending on the structure of their 5' and 3' ends (Feng et al., 2000). Polyadenylation in a cell lysate, followed by purification of RNA, will require inactivation of cellular RNAses so that transcripts are not degraded during the polyadenylation reaction. Optimizing the reaction to work reproducibly in many different bacterial cell lysates would likely be very difficult.

If methods of polyadenylating bacterial mRNAs are to be used in genome-wide expression analysis, it is important that as much as possible, if not all, mRNAs in a population of bacterial mRNA are poly(A) tailed, thereby ensuring that they will be representatively purified by oligo-dT capture and/or templates for the $1^{st}$ strand cDNA synthesis reaction. However, using the standard reaction conditions for commercially available PAP enzymes and synthetic RNA transcripts, the inventors found that only about 90-95% of a transcript could be tailed.

Furthermore, it was also observed that with small mass amounts of RNA, such as those likely to be used for amplification (<100 ng), the tail lengths were extremely long—up to 9 kb in length. The inventors surmise that excessive tail-length could inhibit amplification reactions through several possible mechanisms: (1) reverse transcriptase may dissociate from the template during polymerization through extremely long homopolymeric A tracts; (2) dTTP may be effectively exhausted during $1^{st}$ strand synthesis, slowing the reaction rate; (3) excess poly(A) may itself be detrimental to reaction kinetics; (4) UTP may become limiting during the in vitro transcription step; and/or (5) T7 polymerase may be hindered while incorporating long U tracts at the 5' ends of antisense RNAs (aRNAs).

SUMMARY OF THE INVENTION

The present invention provides methods and compositions for tailing and amplifying a targeted RNA molecule. A targeted RNA molecule may be any non-polyadenylated RNA molecule. Examples of non-polyadenylated RNA include microRNA, siRNA, tRNA, rRNA, synthetic RNA, or non-polyadenylated mRNA, such as mRNA from bacteria or fragments of prokaryotic or eukaryotic mRNAs such as may be encountered in degraded RNA samples. Advantages of the present invention include the ability to efficiently and uniformly tail a targeted RNA and the ability to representatively amplify a population of targeted RNA molecules in a sample.

In a particular aspect, the present invention enables genome-wide expression analysis of bacterial genes. Significantly, the methods and compositions enable genome-wide expression analysis in circumstances where bacterial numbers were previously too low to purify adequate amounts of RNA for DNA microarray analysis or other applications. Such methods and compositions would be particularly useful for the study of bacterial gene expression during host-cell infection.

In one embodiment, the invention provides a method for increasing the efficiency of tailing a targeted RNA in a sample comprising altering the secondary structure of the targeted RNA, and incubating the targeted RNA in the presence of an enzyme that adds a nucleic acid tail under conditions that allow tailing of the targeted RNA. As used herein, "increasing the efficiency of tailing" refers to increasing the percentage of targeted RNA molecules that are tailed during the reaction. In preferred embodiments, at least about 75%, 80%, 85%, or 90% of the targeted RNA molecules in a sample are tailed. More preferably, at least about 95% of the targeted RNA molecules are tailed. Even more preferably, at least about 99% of the targeted RNA molecules are tailed. In certain embodiments, about 95%, 96%, 97%, 98%, 99%, or about 100% of the targeted RNA molecules are tailed.

In another embodiment, the invention provides a method for limiting the length of the tail added to a targeted RNA. The method for limiting the length of the tail added to a targeted RNA comprises one or both of adding a reduced amount of nucleotide or performing the tailing in the presence of substantially no $Mn^{2+}$. Preferably, the majority (i.e., greater that 50%) of tails added to the targeted RNA molecules is between about 10 and about 1000 bases in length. While at least the majority of tails added to the targeted RNA will be between about 10 and about 1000 bases in length, some of the tails added to the targeted RNA may be shorter or longer. In some preferred embodiments, 60% or more, 70% or more, 80% or more, 90% or more, or 95% or more of the tails added to the targeted RNA molecules are between about 10 and about 1000 bases in length. Even more preferably, the majority of tails added to the targeted RNA molecules is between about 20 and about 500 bases in length. In some preferred embodiments, 60% or more, 70% or more, 80% or more, 90% or more, or 95% or more of the tails added to the targeted RNA molecules are between about 20 and about 500 bases in length. The majority of tails added to the targeted RNA molecules may be about 20, 30, 40, 50, 60, 70, 80, 90, 100, 125, 150, 175, 200, 225, 250, 275, 300, 325, 350, 375, 400, 425, 450, 475, or 500 bases in length or any range derivable therein. In certain embodiments, the majority of tails added to the targeted RNA molecules is less than about 500 bases in length. In some preferred embodiments, 60% or more, 70% or more, 80% or more, 90% or more, or 95% or more of the tails added to the targeted RNA molecules are less than about 500 bases in length.

In certain embodiments, the invention provides a method for an optimized tailing reaction. An "optimized tailing reaction" is a reaction that tails about 99% or more of the non-polyadenylated RNA in a sample, and that limits the length of the majority of tails added to the targeted RNA to no more than 500 bases. An optimized tailing reaction comprises altering the secondary structure of the RNAs, limiting the nucleotide concentration in the tailing reaction, using a buffer containing substantially no Mn$^{2+}$, and limiting the tailing reaction time to 5-15 minutes at 37° C.

The amount of nucleotide in the optimized tailing reaction will depend on how much RNA is present in the sample. For example, in samples with RNA amounts in the range of 1-100 ng, the nucleotide preferably is added to a concentration of between about 5-350 µM. More preferably, the nucleotide is added to a concentration of between about 10-100 µM. Even more preferably, the nucleotide is added to a concentration of between about 25-70 µM. For samples with greater amounts of RNA, more nucleotide will be needed. For samples with smaller amounts of RNA, less nucleotide will be needed.

In certain aspects of the invention, altering the secondary structure of the targeted RNA comprises denaturing the targeted RNA. Denaturing the targeted RNA may be accomplished by, for example, heating the targeted RNA. In particular embodiments, the targeted RNA is heated for at least about 10 minutes at a temperature of at least about 70° C. In other aspects of the invention, altering the secondary structure of the targeted RNA comprises adding a single strand binding protein. In a particular aspect, the single strand binding protein is T4 Gene 32 protein.

The target RNA that is tailed and/or amplified by the methods described herein may be any non-polyadenylated RNA, such as microRNA, siRNA, tRNA, rRNA, synthetic RNA, non-polyadenylated mRNA, or degraded mRNA.

As used herein, "tailing" or "tagging" a targeted RNA molecule with a nucleic acid tail means covalently binding a nucleic acid sequence to the targeted RNA molecule. In preferred embodiments, the nucleic acid sequence is covalently bound to the targeted RNA molecule enzymatically. The nucleic acid sequence tail may be added to an end of the targeted RNA molecule. In a specific embodiment, the nucleic acid tail is added to the 3' end of the targeted RNA molecule.

The nucleic acid tail of the present invention may comprise any nucleic acid sequence. The nucleic acid sequence may comprise adenine, guanine, thymine, cytosine, uracil, or analogs thereof. In certain aspects, the targeted RNA molecule may be tailed with more than one tail. For example, an RNA molecule may be tailed first with a homopolymeric sequence, such as poly(A), and then tailed with at least a second homopolymeric sequence, such as poly(U). In another example, an RNA molecule may be tailed with a first sequence, such as a T3 RNA polymerase recognition sequence, and then tailed with at least a second sequence, such as a poly(A) sequence.

In certain aspects, the nucleic acid sequence tail is a homopolymeric sequence, such as a poly(A), poly(T), poly(G), poly(C), or poly(U) sequence. The homopolymeric tail may be of any length, so long as it is capable of hybridizing to a complementary oligonucleotide primer for the initiation of cDNA synthesis. Preferably, the majority of homopolymeric tags is between about 10 and about 1000 bases in length, where a majority is 50% or more, 60% or more, 70% or more, 80% or more, 90% or more, or 95% or more of the tails. Even more preferably, the majority of homopolymeric tails is between about 20 and about 500 bases in length. The majority of homopolymeric tails may be about 20, 30, 40, 50, 60, 70, 80, 90, 100, 125, 150, 175, 200, 225, 250, 275, 300, 325, 350, 375, 400, 425, 450, 475, or 500 bases in length or any range derivable therein. In certain embodiments, the majority of homopolymeric tails is less than 500 bases in length.

In some embodiments, the homopolymeric tail is a poly(A) tail. The poly(A) tail may be of any length, so long as the tail is capable of hybridizing to a complementary oligonucleotide primer for the initiation of cDNA synthesis. In certain aspects, the majority of poly(A) tails is between about 10 and about 1000 adenines in length, where a majority is 50% or more, 60% or more, 70% or more, 80% or more, 90% or more, or 95% or more of the tails. In some aspects, the majority of poly(A) tails is between about 20 and about 500 adenines in length. The majority of poly(A) tails may be about 20, 30, 40, 50, 60, 70, 80, 90, 100, 125, 150, 175, 200, 225, 250, 275, 300, 325, 350, 375, 400, 425, 450, 475, or 500 bases in length or any range derivable therein. In certain embodiments, the majority of poly(A) tails is less than 500 bases in length.

In preferred embodiments, at least about 90% of the targeted RNA molecules in a sample are tailed. More preferably, at least about 95% of the targeted RNA molecules are tailed. Even more preferably, at least about 99% of the targeted RNA molecules are tailed. In certain embodiments, about 95%, 96%, 97%, 98%, 99%, or about 100% of the targeted RNA molecules are tailed.

In one embodiment, the method for limiting the length of the tail added to a targeted RNA comprises adding a reduced amount of a nucleotide to the tailing reaction.

A "reduced amount of a nucleotide" as used herein refers to a nucleotide concentration of 350 µM or lower for RNA amounts in the range of from about 1 ng to about 100 ng. In certain embodiments, the nucleotide is added to a concentration of between about 10-100 µM for RNA amounts in the range of from about 1 ng to about 100 ng. More preferably, the nucleotide is added to a concentration of between about 25-70 µM for RNA amounts in the range of from about 1 ng to about 100 ng. In certain aspects of the invention, the nucleotide is added to a concentration of about 25, 26, 27, 28, 29, 30, 31, 32, 33, 34, 35, 36, 37, 38, 39, 40, 41, 42, 43, 45, 46, 47, 48, 49, 50, 51, 52, 53, 54, 55, 56, 57, 58, 59, 60, 61, 62, 63, 64, 65, 66, 67, 68, 69, or 70 µM for RNA amounts in the range of from about 1 ng to about 100 ng. As will be understood by those of ordinary skill in the art, the nucleotide concentration will vary depending on the amount of RNA in the sample. Nucleotide concentrations between about 25-70 µM are preferred for between about 1-100 ng of RNA. For samples with RNA in amounts greater than 100 ng, more nucleotide may be used. Likewise, for samples with target RNA in amounts less than 1 ng, less nucleotide may be used. Based on these teachings, those of ordinary skill in the art will be able to determine the appropriate concentration of nucleotide to be used for a given sample.

In embodiments where the nucleic acid tail being added to the targeted RNA is a poly(A) tail, the method may further comprise adding ATP. The amount of ATP added will depend on how much target RNA is present in the sample. In one embodiment, the method comprises adding a reduced amount of ATP to the tailing reaction. A "reduced amount of ATP" as used herein refers to ATP added to a concentration of between about 5-350 µM for RNA amounts between about 1-100 ng. More preferably, the ATP is added to a concentration of between about 10-100 µM for RNA amounts between about 1-100 ng. Even more preferably, the ATP is added to a concentration of between about 25-70 µM for RNA amounts between about 1-100 ng. In certain aspects of the invention, the ATP is added to a concentration of about 25, 26, 27, 28, 29, 30, 31, 32, 33, 34, 35, 36, 37, 38, 39, 40, 41, 42, 43, 45, 46, 47, 48, 49, 50, 51, 52, 53, 54, 55, 56, 57, 58, 59, 60, 61, 62, 63, 64, 65, 66, 67, 68, 69, or 70 µM for RNA amounts between about 1-100 ng. For samples with target RNA in amounts greater than 100 ng, more ATP may be used. Likewise, for samples with target RNA in amounts less than 1 ng, less ATP may be used. Based on these teachings, those of ordinary skill in the art will be able to determine the appropriate concentration of ATP to be used for a given sample.

Standard buffers useful for tailing a nucleic acid with a homopolymeric sequence are described in, for example, Eun et al., 1996; and Cao and Sarkar, 1997, both of which are incorporated by reference. The inventors have developed a tailing reaction that limits the length of the tail added to the targeted RNA by employing an "optimized tailing buffer." As used herein, an "optimized tailing buffer" refers to a tailing buffer having substantially no $Mn^{2+}$. In one embodiment, the "optimized tailing buffer" at 1× concentration contains: 50 mM Tris-HCl, pH 8.3; 75 mM KCl; 3 mM $MgCl_2$; and 10 mM DTT.

The "tailing enzyme" of the present invention may be any enzyme capable of adding a nucleic acid tail to a targeted RNA molecule. In preferred embodiments the tailing enzyme is an enzyme capable of synthesizing a homopolymeric tail. Those of ordinary skill in the art are familiar with various enzymes capable of synthesizing homopolymeric tails. For example, poly(A) polymerases such as poly(A) polymerase I of *E. coli* or yeast poly(A) polymerase may be used. Poly(A) polymerases from mammalian or viral sources may also be used. Recombinant poly(A) polymerase enzymes may be used in the methods and compositions of the present invention. Poly(A) polymerase enzymes are described in, for example, Yehudai-Resheff, S. et al. (2000); Mohanty and Kushner (1999); Mohanty and Kushner (2000); Cao and Sarkar (1997); Raynal et al. (1996), all of which are incorporated by reference.

Polynucleotide phosphorylase enzymes could also be used for adding a homopolymeric tail to a targeted RNA molecule. The polyadenylation of RNA using polynucleotide phosphorylase is described in, for example, Engel and Davidson (1978), incorporated by reference.

In certain embodiments of the invention, a nucleotidyl transferase may be used to tail a targeted RNA. Poly(A) polymerase enzymes have sequence similarity with enzymes of the nucleotidyl transferase family. Studies have indicated that some members of the nucleotidyl transferase family have poly(A) polymerase activity (Read and Norbury (2002), incorporated by reference.)

It is specifically contemplated that in some embodiments the tailing enzyme employed to tail the targeted RNA molecule is not a ligase ("non-ligase enzyme").

An RNA sample may be any sample that comprises a targeted RNA molecule. The RNA sample may be obtained from a cell, cell culture, a body fluid, a tissue, or an organ. In certain embodiments, the sample is a fixed sample or a frozen sample, such as a fixed tissue or frozen tissue sample. The sample may be an environmental sample. Examples of environmental samples include soil samples, water samples, and air samples.

In certain embodiments, the RNA sample comprises a mixture of eukaryotic RNA and bacterial RNA. In some embodiments, the RNA sample comprises RNA from more than one bacterial species.

In some embodiments, the methods involve adding a single strand binding protein. Single strand binding proteins are proteins that specifically bind to single stranded nucleic acid molecules. Single strand binding proteins can stabilize single-strand regions of DNA or RNA. Numerous single strand binding proteins are known in the art. In one embodiment, the single strand binding protein is T4 Gene 32 protein. In another embodiment, the single strand binding protein is SSB from *E. coli*. Both T4 Gene 32 protein and SSB are available commercially from USB Corp.

Certain embodiments of the invention involve volume excluding reagents. In one embodiment, a volume excluding reagent is included in the reaction when tailing a targeted RNA molecule. Volume excluding reagents include, for example polyethylene glycol (PEG) and dextran.

In certain embodiments of the invention, the method further comprises depleting DNA from the sample. Methods of depleting DNA or separating DNA from RNA are well known to those skilled in the art. One common approach for depleting DNA is to incubate the sample with DNase. Another approach is an acid phenol:chloroform extraction. Acid phenol:chloroform (e.g., 5:1 phenol:$CHCl_3$; pH 4.7) extraction partitions DNA in to the organic phase. The RNA remains in the aqueous phase and can be subsequently recovered by precipitation. Yet another method for separating DNA from RNA is lithium chloride precipitation. LiCl precipitation selectively precipitates RNA. It inefficiently precipitates DNA, which is discarded in the supernatant. Filter based RNA isolation systems, such as RNAqueous® (Ambion, Austin, Tex.), are also known in the art.

In some embodiments of the invention, the method further comprises depleting polyadenylated mRNA from a sample prior to tailing the targeted RNA. Methods for specifically isolating polyadenylated mRNA from a sample are well known to those of ordinary skill in the art. For example, a common method for isolating polyadenylated mRNA comprises hybridizing the polyadenylated mRNA to a poly(T) oligonucleotide. Typically, the poly(T) oligonucleotide is attached to a surface, such as a column or a bead. After the polyadenylated mRNA is hybridized to the poly(T) oligonucleotide, it can be separated from the sample. For example, if the polyadenylated mRNA is hybridized to the poly(T) oligonucleotide immobilized on a magnetic bead. The beads may then be separated from the sample using a magnet.

In other aspects of the invention, the method further comprises depleting rRNA from the sample. Depending on the composition of the sample, it may be desirable to deplete eukaryotic rRNA, bacterial rRNA, or both. For example, eukaryotic rRNA may hybridized with one or more oligonucleotides complementary to at least a portion of one or more of the 17S rRNA, 18S rRNA, or 28S rRNA. Similarly, bacterial rRNA may be hybridized with one or more oligonucleotides complementary to at least a portion of one or more of the 16S rRNA or 23S rRNA. The hybridization complexes are then removed from the sample with an appropriate capture system. Typically, the oligonucleotides are immobilized on a surface, which enables the removal of the hybridization complexes. MICROBExpress™ and MICROBEnrich™ (Ambion, Austin, Tex.) are examples of commercially available kits for the depletion of rRNA. Methods and compositions for the depletion or rRNA from a sample are described in U.S. application Ser. No. 10/029, 397, which is incorporated by reference.

Depleting rRNA from the sample can enable the relative enrichment of targeted RNA to total RNA in a sample by about or at least about 5, 10, 20, 30, 40, 50, 100, 200, 300, 400, 500, 600, 700, 800, 900, or 1000 fold or any range derivable therein.

In certain aspects, the methods and compositions of the present invention enables the enrichments of targeted RNA in a sample such that about or at least about 50%, 60%, 70%, 80%, 90%, 91%, 92%, 93%, 94%, 95%, 96%, 97%, 98%, 99% or 100%, or any range derivable therein, of the RNA is targeted RNA.

In additional aspects of the invention, the method comprises amplifying the targeted RNA after it is tailed. In certain aspects, amplifying the tailed RNA comprises: hybridizing the tailed RNA with a promoter-oligo-dN primer, where N is a nucleotide complementary to the tail on the targeted RNA; extending the promoter-oligo-dN primer using a reverse transcriptase to form a first strand DNA complementary to the tailed RNA; synthesizing a second strand DNA complementary to the first strand; and transcribing copies of RNA initiated from the promoter-oligo-dN primer using an RNA polymerase, wherein the RNA is complementary to the second strand DNA. The transcribed RNA represents the anti-sense RNA strand.

In some embodiments, the targeted RNA being amplified is poly(A)-tailed. In certain aspects, amplifying the poly(A)-tailed RNA comprises: hybridizing the poly(A)-tailed RNA with a promoter-oligo-dT primer; extending the promoter-oligo-dT primer using a reverse transcriptase to form a first strand DNA complementary to the poly(A)-tailed RNA; synthesizing a second strand DNA complementary to the first strand; and transcribing copies of RNA initiated from the promoter-oligo-dT primer using an RNA polymerase, wherein the RNA is complementary to the second strand DNA. The transcribed RNA represents the anti-sense RNA strand.

In some embodiments, the methods and compositions enable at least a 500, 750, 1,000, 1,250, 1,500, 1,750, 2,000, 2,250, 2,500, 2,750, 3,000, 4,000, 5,000, 6,000, 7,000, 8,000, 9,000, 10,000, or 20,000 fold or more amplification of the targeted RNA.

The RNA polymerase may be, for example, a T bacteriophage RNA polymerase or an SP6 RNA polymerase. Preferably, the T bacteriophage RNA polymerase is T7 RNA polymerase or T3 RNA polymerase.

In some preferred embodiments the promoter-oligo-dT primer is a T7-oligo-dT, T7-oligo-dTV, or T7-oligo-dTVN. In some embodiments, the T7-oligo-dT is T7-$dT_{24}$VN. In one preferred embodiment the T7-oligo-dT sequence is 5'-GGTAATACGACTCACTATAGGGAGAAGAG$(T)_{24}$VN-3' (SEQ ID NO. 1).

It will be obvious to those of skill in the art that any reverse transcriptase may be used in the present invention. In preferred embodiments, the reverse transcriptase is Moloney murine leukemia virus (MMLV) reverse transcriptase or avian myeloblastosis virus (AMV) reverse transcriptase. The reverse transcriptase may be a mutant reverse transcriptase, as long as the mutants retain cDNA synthesizing activity. Examples of reverse transcriptase mutants include those with reduced or absent RnaseH activity (e.g., Superscript™ II, Superscript™ III, and ThermoScript™ (Invitrogen)) and those with enhanced activity at higher temperatures (Superscript™ III and ThermoScript™ (Invitrogen)). In one preferred embodiment the reverse transcriptase is Arrayscript™ (Ambion), which is a mutant MMLV with reduced RnaseH activity.

In some embodiments, the invention comprises using a targeted RNA for expression analysis. Methods of gene expression analysis are well known in the art. In preferred embodiments, the expression analysis comprises hybridizing the targeted RNA to a microarray. The expression analysis may be performed on either amplified or unamplified, targeted RNA. In a preferred embodiment, amplified RNA is used for expression analysis.

In certain aspects of the invention, the targeted RNA and/or amplified RNA are labeled. Labeling the targeted RNA and/or amplified RNA facilitates the detection of the molecules in applications such as expression analysis. A number of different labels may be used in the present invention such as fluorophores, chromophores, radiophores, enzymatic tags, antibodies, chemiluminescence, electroluminescence, and affinity labels. Those of skill in the art are familiar with methods for labeling nucleic acids and will recognize that these and other labels not mentioned herein can be used with success in this invention.

Examples of affinity labels include, but are not limited to the following: an antibody, an antibody fragment, a receptor protein, a hormone, biotin, DNP, or any polypeptide/protein molecule that binds to an affinity label.

Examples of enzyme tags include enzymes such as urease, alkaline phosphatase or peroxidase to mention a few. Colorimetric indicator substrates can be employed to provide a detection means visible to the human eye or spectrophotometrically, to identify specific hybridization with complementary nucleic acid-containing samples. All of these examples are generally known in the art and the skilled artisan will recognize that the invention is not limited to the examples described above.

Examples of fluorophores include, but are not limited to the following: Alexa 350, Alexa 430, AMCA, BODIPY 630/650, BODIPY 650/665, BODIPY-FL, BODIPY-R6G, BODIPY-TMR, BODIPY-TRX, Cascade Blue, Cy2, Cy3, Cy 3.5, Cy5, Cy5.5, Cy7, 6-FAM, Fluoroscein, HEX, 6-JOE, Oregon Green 488, Oregon Green 500, Oregon Green 514, Pacific Blue, REG, Rhodamine Green, Rhodamine Red, ROX, TAMRA, TET, Tetramethylrhodamine, lissamine, phycoerythrin, FluorX, and Texas Red.

In some embodiments, the invention provides a method for amplifying bacterial mRNA from a sample comprising bacterial cells of a single species or bacterial cells of multiple species comprising: isolating RNA from the sample; tailing the bacterial mRNA; and amplifying the bacterial mRNA.

In other embodiments, the invention provides a method for amplifying bacterial mRNA from a sample comprising bacterial cells of a single species or bacterial cells of multiple species and eukaryotic cells comprising: isolating RNA from the sample; depleting polyadenylated mRNA from the isolated RNA; depleting rRNA from the isolated RNA; tailing the bacterial mRNA; and amplifying the bacterial mRNA.

In some embodiments, the invention provides a method for amplifying bacterial mRNA from a sample comprising bacterial cells and eukaryotic cells comprising: isolating RNA from the sample; depleting polyadenylated mRNA from the isolated RNA; depleting rRNA from the isolated RNA; tailing the bacterial mRNA; and amplifying the bacterial mRNA.

In other embodiments, the invention provides a method for analyzing bacterial mRNA expression in a sample comprising bacterial RNA and eukaryotic RNA comprising: isolating the bacterial RNA and the eukaryotic RNA from the sample to form an RNA composition; depleting polyadenylated mRNA and rRNA from the RNA composition resulting in a relative enrichment of bacterial mRNA in the RNA composition; polyadenylating the bacterial mRNA; and amplifying the bacterial mRNA, wherein the amplified bacterial mRNA is used for expression analysis.

In certain embodiments, the method comprises stabilizing RNA in the sample. Any method of stabilizing RNA in a sample that is known in the art may be used in the practice of the present invention. Commercially available products for stabilizing RNA include RNAlater® from Ambion (Austin, Tex.) and RNAprotect™ Bacteria Reagent from Qiagen (Valencia, Calif.). Examples of other methods for stabilizing RNA include phenol/EtOH mixtures (Eriksson et al., 2003), incorporated by reference), and acetone/EtOH mixtures.

In some embodiments, the present invention provides an improvement in a method for polyadenylating bacterial mRNA, wherein the improvement comprises altering the secondary structure of the mRNA prior to incubating the mRNA with a poly(A) polymerase and polyadenylating the mRNA in the presence of substantially no $Mn^{2+}$. Altering the secondary structure of the mRNA may comprise, for example, denaturing the mRNA or adding a single strand binding protein.

Other aspects of the invention provide kits. In certain embodiments, the kit, in suitable container means, comprises: a poly(A) polymerase; ATP; an optimized tailing buffer; and a control RNA.

In certain embodiments, the kit further comprises one or more of: an RNA polymerase; a single strand binding protein; ethylenediaminetetraacetic acid (EDTA); a reverse transcriptase; a first strand buffer; a promoter-oligo-dT primer; a dNTP mix; a ribonuclease inhibitor; a second strand buffer; a DNA polymerase; RNase H; nuclease free water; an RNA polymerase reaction buffer; ATP; CTP; GTP; UTP; TTP; DNase I; a cDNA binding buffer; a cDNA wash buffer; an aRNA binding buffer; an aRNA wash buffer; an elution solution; an aRNA filter cartridge; a cDNA filter cartridge; or collection tubes.

In some embodiments, the poly(A) polymerase is poly(A) polymerase I of *E. coli* or yeast poly(A) polymerase.

In certain embodiments, the promoter-oligo-dT primer promotes transcription by a T bacteriophage RNA polymerase, such as T7 RNA polymerase or T3 RNA polymerase. In other embodiments, the promoter-oligo-dT primer is an SP6-oligo-dT primer. In a preferred embodiment the promoter-oligo-dT primer is a T7-oligo-dT primer. In certain embodiments the T7-oligo-dT primer is T7-dT$_{24}$VN.

The RNA polymerase may be, for example, T7 RNA polymerase, T3 RNA polymerase, or SP6 RNA polymerase.

Non-limiting examples of single strand binding proteins include T4 Gene 32 and *E. coli* SSB. A non-limiting example of a ribonuclease inhibitor is placental ribonuclease inhibitor. Examples of DNA polymerases include *E. coli* DNA polymerase and T4 DNA polymerase.

It is contemplated that any method or composition described herein can be implemented with respect to any other method or composition described herein.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 shows an Agilent Bioanalyzer electropherogram depicting the extent of polyadenylation of a synthetic GAPDH transcript that was polyadenylated using poly(A) polymerase I. The untailed transcript in the control reaction (no poly(A) polymerase I) is ~315 nucleotides. The majority of the tailed transcript is ~570 nucleotides. However, some transcripts are tailed to greater lengths.

FIG. 2 shows an Agilent Bioanalyzer electropherogram depicting the extent of polyadenylation for reactions with or without $MnCl_2$, and with reaction times of 5, 10, or 15 minutes. When the reaction is performed with $MnCl_2$ at a concentration of 2.5 mM, tail length extends from about 0.5 Kb to beyond 6 Kb. When $MnCl_2$ is not added to the reaction, tail length is reduced to a median size of about 150 nucleotides. While incubation time has some effect on tail length, it is small relative to the $MnCl_2$ effect.

DESCRIPTION OF ILLUSTRATIVE EMBODIMENTS

A. The Present Invention

Figure 1:
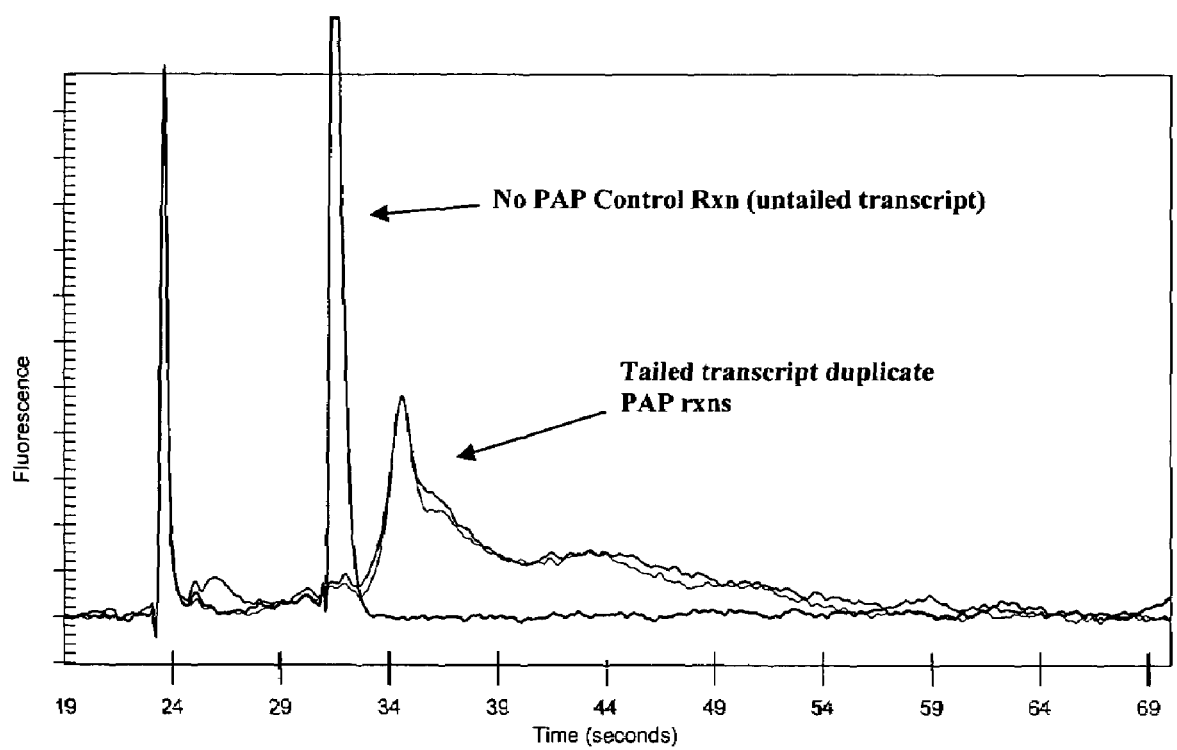
FIG. 1.

The present invention provides methods and compositions for tailing and amplifying a targeted RNA molecule. A targeted RNA molecule may be any non-polyadenylated RNA. Examples of non-polyadenylated RNA include microRNA, siRNA, tRNA, rRNA, synthetic RNA, or non-polyadenylated mRNA, such as mRNA from bacteria or degraded mRNA from prokaryotic or eukaryotic organisms. Advantages of the present invention include the ability to efficiently and uniformly tail a targeted RNA and the ability to representatively amplify a population of targeted RNA molecules in a sample. The ability to representatively amplify a population of targeted RNA molecules in a sample provides a significant advantage over the prior art in that it enables the study of samples containing RNA molecules in mass amounts previously too low to be analyzed.

In one aspect, the present invention provides methods and compositions that enable genome-wide expression analysis of bacterial genes. Significantly, the methods enable genome-wide expression analysis in circumstances where bacterial numbers were previously too low to purify adequate amounts of RNA for DNA microarray analysis or other applications. Such methods are particularly useful for the study of bacterial gene expression during host-cell infection, and for the study of gene expression in bacteria present in environmental samples.

In one embodiment, the present invention provides a method for genome-wide expression analysis that employs an "optimized" polyadenylation reaction followed by first strand cDNA synthesis initiated from a T7-oligo-dT primer, and then transcription of aRNA using an Eberwine type amplification reaction with a mutant MMLV RT. The aRNA is then used for microarray analysis.

An "optimized" polyadenylation reaction is a reaction that polyadenylates about 99% or more of the non-polyadenylated RNA in a sample, and that limits the length of the majority of poly(A) tags to no more than 500 bases. An "optimized" polyadenylation reaction comprises denaturing the RNAs, limiting the ATP concentration in the poly(A) polymerase reaction, using a buffer lacking $Mn^{2+}$, and limiting the poly(A) polymerase reaction time to 5-15 minutes at 37° C. In some embodiments, the "optimized" polyadenylation reaction may comprise adding a single strand binding protein to the reaction.

The amount of ATP in the "optimized" polyadenylation reaction will depend on how much RNA is present in the sample. For example, in samples with RNA amounts in the range of 1-100 ng, the ATP preferably is added to a concentration of between about 5-350 µM. More preferably, the ATP is added to a concentration of between about 10-100 µM. Even more preferably, the ATP is added to a concentration of between about 25-70 µM. For samples with greater amounts of RNA, more ATP will be needed. For samples with smaller amounts of RNA, less ATP will be needed.

In other embodiments, the present invention provides kits. In a preferred embodiment, the kits comprise, in suitable container means, a poly(A) polymerase, ATP, a control RNA, and an optimized tailing buffer.

B. RNA

There are several types of naturally occurring RNA molecules including messenger RNA (mRNA), transfer RNA (tRNA), ribosomal RNA (rRNA), microRNA, and siRNA. These molecules performs many different functions in the cell. mRNA, which conveys information from the nucleus to the cytoplasm in eukaryotes, is the most intensely studied. Several molecular biology procedures use purified mRNA as starting material or are designed to work primarily with mRNA. These procedures include: cDNA synthesis (for library construction, RT-PCR analysis, or 5' end analysis through primer extension); Northern blot analysis; ribonuclease protection assays; screening procedures involving in vitro translation; and gene expression analysis with microarrays.

There are several existing procedures to purify RNA from various biological samples. However, mRNA represents only 1-5% of the mass of total RNA (Sambrook, 2001). Of the remainder, the major RNA species is ribosomal RNA (rRNA), constituting 80% or more of total RNA mass (Sambrook et al., 1989 and 2001). Although the total RNA isolated from cells can sometimes be used for the abovementioned procedures, usually a preliminary purification of mRNA from total RNA is often preferred, if not required. This is especially true if the particular mRNA being sought or targeted is in low abundance (0.5% or less of the mRNA population). The presence of rRNA can interfere in the detection of mRNA by Northern blotting, RNase protection assays, differential display analysis, and expression profiling by gene arrays, especially if the target being analyzed is in low abundance. Often, the mRNA from scientifically interesting genes falls into this category.

In eukaryotic cells, mRNAs are polyadenylated at their 3'-termini, unlike rRNAs and tRNAs. The poly(A) tails of eukaryotic mRNAs usually consist of about 200 adenosyl residues and allow them to be purified based on hybridization to oligo(dT) nucleotides. In contrast, bacterial mRNAs are not uniformly polyadenylated and therefore cannot be purified by oligo(dT) hybridization. The lack of an efficient method to purify and/or amplify bacterial mRNA has hampered in vivo whole-genome expression analyses. Genome-wide expression analysis of bacterial genes is made even more difficult in circumstances where the pool of bacterial mRNA is limited, such as in host-cell infection or in some environmental samples.

In addition to bacterial mRNA, the methods and compositions of the present invention may be used in conjunction with any non-polyadenylated RNA including, for example, siRNA, microRNA, tRNA, rRNA, synthetic RNA, and degraded mRNA. Methods and compositions relating to siRNA molecules are described, for example, in U.S. application Ser. Nos. 10/298,480, 10/360,772, 10/460,775, and 10/355,820, each of which in incorporated herein by reference. Methods and compositions relating to isolating, manipulating, and using microRNA molecules are described, for example, in U.S. application Ser. No. 10/667, 126 and U.S. Application 60/575,743, each of which is incorporated herein by reference.

1. Stabilizing RNA

Obtaining high quality, intact RNA is important for quantitative and qualitative analysis of RNA expression. To obtain high quality RNA it is necessary to minimize the activity of RNase liberated during cell lysis and to prevent RNA degradation from other sources. This is normally accomplished by using isolation methods that disrupt tissues and inactivate or inhibit RNases simultaneously.

For specimens low in endogenous ribonuclease, isolation protocols commonly use extraction buffers containing detergents to solubilize membranes, and inhibitors of RNase such as placental ribonuclease inhibitor or vanadylribonucleoside complexes. RNA isolation from more challenging samples, such as intact tissues or cells high in endogenous ribonuclease, requires a more aggressive approach. In these cases, the tissue or cells are quickly homogenized in a powerful protein denaturant (usually guanidinium isothiocyanate), to irreversibly inactivate nucleases and solubilize cell membranes. If a tissue sample can not be promptly homogenized, it must be rapidly frozen by immersion in liquid nitrogen, and stored at −80° C. Samples frozen in this manner should not be thawed prior to RNA isolation or the RNA will be rapidly degraded by RNase liberated during the cell lysis that occurs during freezing.

RNA preservation reagents that can protect the RNA in a tissue or cell sample from nucleases at temperatures above the freezing point are also know in the art, and are described, for example, in U.S. Pat. Nos. 6,528,641 and 6,204,375, incorporated herein by reference.

2. Isolation of RNA

Methods of isolating RNA are known to those of skill in the art, and it is contemplated that any RNA isolation or purification scheme known in the art could be used in the context of the present invention. For example, Filter-based methods for the isolation of RNA are also known in the art. One example is Ambion's RNAqueous® Technology. RNAqueous® is a rapid, filter-based RNA isolation system that does not require the use of phenol, chloroform or other toxic organic chemicals.

In addition, commercially available kits such as Ambion's RiboPure™ RNA Isolation Kit, RiboPure™-Bacteria RNA Isolation Kit, and RiboPure™-Yeast RNA Isolation Kit may be used to isolate RNA. Additional methods for isolating RNA are described, for example, in U.S. application Ser. No. 09/854,412, incorporated herein by reference. Methods and compositions for isolating RNA from fixed tissues are described, for example, in U.S. Application 60/490,325, incorporated herein by reference. It is also contemplated that the chemical synthesis of RNA in situ can be used to prepare RNA.

3. Separation of DNA and RNA

In certain embodiments of the invention, it is desirable to remove DNA from RNA samples. DNA contamination can interfere with the quantitative analysis of mRNA. For example, DNA contamination can cause false positives in quantitative RT-PCR.

Methods of DNA removal from RNA samples are known to those skilled in the art. Examples of common methods include DNase digestion, acid phenol:chloroform extraction, and LiCl precipitation.

DNase is an endonuclease that cleaves DNA. It must be inactivated or removed from the reaction prior to PCR, otherwise, it may digest newly amplified DNA. Acid phenol:chloroform (5:1 phenol:$CHCl_3$; pH 4.7) extraction partitions DNA in to the organic phase. The RNA remains in the aqueous phase and can be subsequently recovered by precipitation. LiCl is a selective precipitant of RNA. It inefficiently precipitates DNA, which is discarded in the supernatant.

4. Separation of rRNA from mRNA

Ribosomal RNAs can make up as much as 80% or more of the total RNA in a sample. It is often desirable to separate mRNA from rRNA because rRNA can adversely affect the quantitative analysis of mRNA. For example, the presence of rRNA can increase background in mRNA samples, resulting in variations in mRNA concentration between samples and decreasing the efficiency of cDNA probe synthesis. In eukaryotic organisms, mRNAs have a poly(A) tail at the 3' end. This can be used to separate these molecules away from rRNA and other non-mRNA species that lack this "polyA tail." Bacterial mRNA, however, are not uniformly polyadenylated and consequently cannot be separated from rRNA based on this property.

One approach to separating rRNA from mRNA is to deplete the rRNA from the sample. One example, is the hybridization of rRNA molecules using oligonucleotides homologous to the 17S rRNA, 18S rRNA, or 28S rRNA in the case of eukaryotic rRNAs, or to the 16S rRNA or 23S rRNA in the case of bacterial rRNA. The oligonucleotides are designed such that they can be "captured" and the hybridization product removed from the sample. For example, the oligonucleotides may be immobilized on a surface such as a column or a bead. MICROBExpress™ and MICROBEnrich™ (Ambion, Austin, Tex.) are examples of commercially available kits for the depletion of rRNA. Methods and compositions for the depletion or rRNA from a sample are described in U.S. application Ser. No. 10/029,397, which is incorporated by reference.

5. Separation of Polyadenylated mRNA from Non-Polyadenylated mRNA

In eukaryotic organisms, one trait shared by all mRNAs is the presence on the 3' end of a stretch of tens to hundreds of adenine (A) residues. This has been used as a means for separating these molecules away from rRNA and other non-mRNA species that lack this "polyA tail." The standard protocol for the selection of polyA+ RNA is based on the method of Aviv and Leder (1972), wherein a short stretch of DNA consisting solely of thymidine (T) residues ('oligo-dT') is affixed to an insoluble matrix. The original procedure used oligo-dT covalently linked to cellulose poured into a column. This is then used as a selective immobilization matrix for mRNA in the sample by setting up conditions that favor formation of RNA-DNA double strands. The total RNA sample is applied to the column in an appropriate salt buffer (originally 0.5 M KCl in 10 mM Tris, pH 7.5), encouraging hybridization to the polyA stretches found solely at the 3' ends of mRNA. The column is then subjected to extensive washing with the application buffer (containing 0.5 M KCl), then a lower-ionic-strength solution (0.1 M KCl), followed by elution of mRNA with 10 mM Tris (pH 7.5). Subsequent modifications on this original procedure have retained the basic process of hybridization to immobilized oligo-dT in approximately 0.5 M salt, but have changed the format from columns to batch procedures to allow the procedure to be performed faster and have used NaCl or LiCl as the salts.

Further changes have been the replacement of cellulose with plastic or glass beads as the immobilization matrix, some of which are impregnated with ferrous material giving them a magnetic quality. This magnetic quality allows such magnetic beads, as they are referred to, to be batch isolated on magnetic stands rather than requiring gravity or centrifugal force to pellet or filter separate. A further wrinkle in the procedure is the use of a biotin-streptavidin linkage in the connection between oligo-dT and bead, where the oligo is biotinylated and the bead is covalently coupled to streptavidin. The hybridization can be performed in solution with this procedure, linking the oligo-dT-mRNA hybrids to the beads in a subsequent step.

Bacteria, however, lack the relatively stable poly(A) tails found on eukaryotic messages. The inventors have exploited this difference between eukaryotic mRNA and bacterial mRNA to efficiently separate the two populations of mRNA from mixed samples. By selectively hybridizing mRNA with poly(A) tails to immobilized oligo-dT molecules, the eukaryotic mRNA can be depleted from a sample while the bacterial mRNA remains in the sample.

6. Nucleic Acid Tails

The present invention provides methods for tailing a targeted RNA molecule in a sample with a nucleic acid tail. The nucleic acid tail may be any nucleic acid sequence. For example, the nucleic acid tail may be a homopolymeric sequence, such as a poly(A), poly(T), poly(G), poly(C), or poly(U) sequence.

Methods for adding nucleic acid sequences to RNA molecules are known to those of skill in the art. For example, to add a poly(A) sequence to the 3' end of an RNA, one could use a poly(A) polymerase, such as poly(A) polymerase I of *E. coli* or yeast poly(A) polymerase. The present invention provides improvements over prior art methods of polyadenylating mRNA molecules by providing conditions that increase the efficiency of polyadenylation and limit the size of the poly(A) tails.

Seemingly straightforward and simple, the polyadenylation of complex RNA populations is actually a quite complicated reaction. For polyadenylating bacterial mRNAs, the inventor used purified poly(A) polymerase I (PAP I) enzyme of *E. coli*. PAP I or PAP adds AMP to 3' ends of RNA molecules using ATP as a donor. The efficiency of PAP has been found to vary with different substrate RNAs. RNAs with 3' end nucleotides that are paired, such as in a hairpin, are less efficiently polyadenylated (Feng and Cohen, 2000). The enzyme uses an ordered bi-bi kinetic mechanism and adds As distributively (Eun, 1996). Initiation and elongation occur at different rates, and the enzyme dissociates from the primer after every step.

To ensure representative amplification of a population of bacterial mRNAs, it is important that essentially all mRNAs in a population of bacterial mRNA are poly(A) tailed. However, using standard reaction conditions for commercially available PAP enzymes and synthetic RNA transcripts, the inventor found that only about 90-95% of a transcript could be tailed.

Another drawback to using the standard reaction conditions for commercially available PAP enzymes was that for small mass amounts of RNA, such as those likely to be used for amplification (<100 ng), the tail lengths were extremely long—up to 9 kb in length. Excessive tail-length could inhibit amplification reactions through several possible mechanisms: (1) reverse transcriptase may dissociate from the template during polymerization through extremely long homopolymeric A tracts; (2) dTTP may be effectively exhausted during $1^{st}$ strand synthesis, slowing the reaction rate; (3) excess poly(A) may itself be detrimental to reaction kinetics; (4) UTP may become limiting during the in vitro transcription step; and/or (5) T7 polymerase may be hindered while incorporating long U tracts at the 5' ends of antisense RNAs (aRNAs).

Limiting tail lengths and ensuring that all of the targeted RNA is tailed are intricately linked. Achieving one of the goals usually adversely affects the other. To optimize this procedure, the inventors altered numerous reaction constituents and parameters and tested novel reaction components and conditions.

Two reaction modifications: (1) altering the secondary structure of the RNA by either adding a single stranded binding protein (e.g., T4 Gene 32 protein) or denaturing the RNA prior to its addition to the PAP reaction; and (2) removing $Mn^{2+}$ from the "standard" PAP reaction buffer enabled the tailing of essentially 99-100% of a transcript. This was verified by analyzing reactions on RNA LabChips and by quantifying radiolabeled transcripts before and after tailing with a phosphorimager. Both methods indicated that <1% of the untailed transcript remains following the PAP reaction.

Limiting the size of the poly(A)-tails appended to mRNAs was accomplished by drastically reducing the ATP concentration in the reaction to 25-70 µM for target RNA amounts in the range of 1-100 ng and by reducing the reaction time to 5-15 min at a temperature of 37° C.

The improved method of polyadenylating bacterial mRNA provided by the present invention, which ensures that essentially all of the transcript is tailed and that limits tail lengths, enables genome-wide expression analysis of bacterial genes by enabling representative amplification of bacterial mRNA molecules. Moreover, the methods and composition of the present invention can be applied to any non-polyadenylated RNA.

7. Amplification of Antisense RNA

In some embodiments, the present invention provides methods and compositions for the amplification of targeted RNA molecules. Amplification of targeted RNA molecules is desirable when the amount of targeted RNA in a sample is too low for microarray analysis or other applications.

In certain aspects, the target RNA is amplified by the processive synthesis of multiple RNA molecules from a single cDNA template, which results in amplified, antisense RNA (aRNA). Methods for the synthesis of aRNA are described in U.S. Pat. Nos. 5,545,522, 5,716,785, and 5,891, 636 all of which are incorporated herein by reference.

In typical embodiments, these methods involve the incorporation of an RNA polymerase promoter into a cDNA molecule by priming cDNA synthesis with a primer complex comprising a synthetic oligonucleotide containing the promoter. Following synthesis of double-stranded cDNA, a reverse transcriptase is added, and antisense RNA is transcribed from the cDNA template. The amplification, which will typically be at least about 500-fold, but may be at least about 1,000-, 5,000-, 10,000-, 15,000-, or 20,000-fold or more, can be achieved from nanogram quantities or less of cDNA, and is economical and simple to perform under standard molecular biology laboratory conditions.

One advantage that the processive synthesis of aRNA has over PCR is that only one region of shared sequence need be known to synthesize aRNA; PCR generally requires that shared sequences be known both 5'- and 3'- to the region of interest, and that these flanking regions be sufficiently close to allow efficient amplification.

The synthesis of aRNA is useful for amplifying sequences of interest from small amounts of nucleic acid. The aRNA amplification is uniform among individual sequences, and thus, it is useful in estimating relative levels of representation of a given sequence relative to other sequences within a population. Such quantitative resolution finds use in a variety of application. Of particular interest is the genome-wide expression analysis of bacterial genes.

For example, aRNA can be amplified from limited amounts of clinical material to allow pathogen-specific sequences to be identified. In a preferred embodiment, the present invention polyadenylates bacterial mRNAs, and then uses an amplification primer with a polythymidylate region that recognizes the commonly shared poly(A) tail. Preferably the promoter region of the amplification primer is derived from the SP6, T3, or T7 phage. The RNA polymerase used for the transcription must be capable of operably binding to the particular promoter region employed in the promoter-primer complex. A preferred RNA polymerase is that found in bacteriophages, in particular T3 and T7 phages.

8. Hybridization

As used herein, "hybridization", "hybridizes" or "capable of hybridizing" is understood to mean the forming of a double or triple stranded molecule or a molecule with partial double or triple stranded nature. The term "anneal" as used herein is synonymous with "hybridize." The term "hybridization", "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those conditions that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.15 M NaCl at temperatures of about 50° C. to about 70° C. Alternatively, stringent conditions may be determined largely by temperature in the presence of a TMAC solution with a defined molarity such as 3M TMAC. For example, in 3 M TMAC, stringent conditions include the following: for complementary nucleic acids with a length of 15 bp, a temperature of 45° C. to 55° C.; for complementary nucleotides with a length of 27 bases, a temperature of 65° C. to 75° C.; and, for complementary nucleotides with a length of >200 nucleotides, a temperature of 90° C. to 95° C. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride (TMAC), tetraethyl ammonium chloride (TEAC), or other salts or solvent(s) in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions," and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suite a particular application.

9. Nucleic Acid Arrays

Because the present invention provides efficient methods and compositions for the purification and global amplification of target RNA molecules from complex RNA mixtures or from samples with limited amounts of RNA, it enables the detection of previously undetectable RNA molecules with nucleic acid arrays. In a particular embodiment, the invention provides methods and compositions for the analysis of bacterial mRNA expression using nucleic acid arrays. The term a "nucleic acid array" refers to a plurality of probe elements, each probe element comprising one or more nucleic acid molecules immobilized on one or more solid surfaces to which sample nucleic acids can be hybridized.

Microarrays are known in the art and consist of a surface to which probes that correspond in sequence to gene products (e.g., cDNAs, mRNAs, cRNAs, polypeptides, and fragments thereof), can be specifically hybridized or bound at a known position. In one embodiment, the microarray is an array (i.e., a matrix) in which each position represents a discrete binding site for an RNA, and in which binding sites are present for products of most or almost all of the genes in the organism's genome. In a preferred embodiment, the "binding site" (hereinafter, "site") is a nucleic acid or nucleic acid analogue to which a particular cognate cDNA or aRNA can specifically hybridize. The nucleic acid or analogue of the binding site can be, e.g., a synthetic oligomer, a full-length cDNA, a less-than full length cDNA, or a gene fragment. A microarray may contain binding sites for products of all or almost all genes in the target organism's genome, but such comprehensiveness is not necessarily required.

The nucleic acid or analogue is attached to a solid support, which may be made from glass, plastic (e.g., polypropylene, nylon), polyacrylamide, nitrocellulose, or other materials. A preferred method for attaching the nucleic acids to a surface is by printing on glass plates, as is described generally by Schena et al., 1995. See also DeRisi et al., 1996; Shalon et al., 1996; Schena et al., 1996. Each of these articles is incorporated by reference in its entirety.

Other methods for making microarrays, e.g., by masking (Fodor et al., 1991; Maskos and Southern, 1992), may also be used. In principal, any type of array, for example, dot blots on a nylon hybridization membrane (see Sambrook et al., 1989, which is incorporated in its entirety for all purposes), could be used, although, as will be recognized by those of skill in the art, very small arrays will be preferred because hybridization volumes will be smaller.

Labeled cDNA is prepared from mRNA by oligo dT-primed or random-primed reverse transcription, both of which are well known in the art. Reverse transcription may be carried out in the presence of a dNTP conjugated to a detectable label, most preferably a fluorescently labeled dNTP. Alternatively, isolated mRNA can be converted to labeled antisense RNA synthesized by in vitro transcription of double-stranded cDNA in the presence of labeled dNTPs (Lockhart et al., 1996, which is incorporated by reference in its entirety for all purposes). In alternative embodiments, the cDNA or aRNA probe can be synthesized in the absence of detectable label and may be labeled subsequently, e.g., by incorporating biotinylated dNTPs or rNTP, or some similar means (e.g., photo-cross-linking a psoralen derivative of biotin to RNAs), followed by addition of labeled streptavidin (e.g., phycoerythrin-conjugated streptavidin) or the equivalent. Alternatively, cDNA or aRNA can be labeled indirectly by incorporation of 5-(3-aminoallyl) dNTPs or rNTPs to provide a amine reactive group for subsequent addition of label with any moiety bearing an N-Hydroxysuccinimide (NHS) ester.

Fluorescently labeled probes can be used, including suitable fluorophores such as fluorescein, lissamine, phycoerythrin, rhodamine (Perkin Elmer Cetus), Cy2, Cy3, Cy3.5, Cy5, Cy5.5, Cy7, FluorX (Amersham) and others (see, e.g., Kricka, 1992). It will be appreciated that pairs of fluorophores are chosen that have distinct emission spectra so that they can be easily distinguished. In another embodiment, a label other than a fluorescent label is used. For example, a radioactive label, or a pair of radioactive labels with distinct emission spectra, can be used (see Zhao et al., 1995; Pietu et al., 1996).

The analysis of microarray data may be accomplished using methods of statistical analysis known to those skilled in the art. For example, clustering analysis is commonly used for interpretation of microarray data. It provides both a visual representation of complex data and a method for measuring similarity between experiments. Some widely used methods for clustering microarray data include: hierarchical, K-means, and self-organizing map.

C. Kits

Any of the compositions described herein may be comprised in a kit. In a non-limiting example the kit, in suitable container means, comprises: a poly(A) polymerase; ATP; an optimized tailing buffer; and a control RNA. In certain embodiments, the kit further comprises one or more of: an RNA polymerase; a single strand binding protein; ethylenediaminetetraacetic acid (EDTA); a reverse transcriptase; a first strand buffer; a promoter-oligo-dT primer; a dNTP mix; a ribonuclease inhibitor; a second strand buffer; a DNA polymerase; RNase H; nuclease free water; an RNA polymerase reaction buffer; ATP; CTP; GTP; UTP; TTP; DNase I; a cDNA binding buffer; a cDNA wash buffer; an aRNA binding buffer; an aRNA wash buffer; an elution solution; an aRNA filter cartridge; a cDNA filter cartridge; or collection tubes. In certain embodiments the kit may also include, an rRNA depleting agent, a DNA depleting agent, labeling agents, or components for isolating poly(A) mRNA.

In some embodiments the kit includes one or more of the following, but is not limited to these components or their precise compositions: a control RNA (e.g., E. coli total RNA); EDTA; poly(a) polymerase (e.g., E. coli PAP); 10× optimized tailing buffer (500 mM Tris-HCl, pH 8.3; 750 mM KCl; 30 mM MgCl$_2$; 100 mM DTT); ATP; reverse transcriptase (e.g., AMV-RT, MMLV, Arrayscript MMLV, or other mutant reverse transcriptase); 10× first strand buffer (500 mM Tris-HCl, pH 8.0; 750 mM KCl; 30 mM MgCl$_2$; 100 mM DTT); first strand primer (e.g., a T7-oligo-d(T) primer); dNTP mix (5 mM dATP, 5 mM dCTP, 5 mM dGTP, 5 mM dTTP in 10 mM Tris, pH 8.0); ribonuclease inhibitor (e.g., placental ribonuclease inhibitor); 10× second strand buffer (150 mM Tris, pH 7.0; 850 mM KCl; 50 mM MgCl$_2$; 50 mM (NH$_4$)$_2$SO$_4$); DNA polymerase (e.g., *E. coli* DNA polymerase or T4 DNA polymerase); RNase H; nuclease free water; T7 enzyme mix (T7 RNA polymerase, RNase inhibitor protein (RIP), inorganic pyrophosphatase (IPP), SUPERaseIn™); 10×T7 reaction buffer (400 mM Tris, pH 8.0; 240-260 mM MgCl$_2$; 20 mM spermidine; 100 mM DTT); CTP; GTP; UTP; DNase I; cDNA binding buffer (25 mM Tris, pH 7.0; 5.5 M guanidium thiocyanate); cDNA wash buffer (80% ethanol); aRNA binding buffer (4 M GITC; 0.5% N-lauryl sarcosine; 25 mM Na citrate, pH 7.2; 0.1 M 2-mercaptoethanol); aRNA wash buffer (80% ethanol); elution solution (0.1 mM EDTA, pH 8.0); aRNA filter cartridges; 2 ml tubes; and cDNA filter cartridges. It is contemplated that any of these components can be included in a kit with any of the other components.

The kits may comprise suitably aliquoted nucleic acid compositions of the present invention, whether labeled or unlabeled, as may be used to isolate, deplete, or separate a targeted nucleic acid. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. The kits of the present invention also will typically include a means for containing the nucleic acids, and any other reagent containers in close confinement for commercial sale. Such containers may include cardboard containers or injection or blow-molded plastic containers into which the desired vials are retained.

When the components of the kit are provided in one or more liquid solutions, the liquid solution is an aqueous solution, with a sterile aqueous solution being preferred.

However, the components of the kit may be provided as dried powder(s). When reagents and/or components are provided as a dry powder, the powder can be reconstituted by the addition of a suitable solvent. It is envisioned that the solvent may also be provided in another container means.

The container means will generally include at least one vial, test tube, flask, bottle, syringe and/or other container means, into which the nucleic acid formulations are placed, preferably, suitably allocated. The kits may also comprise a second container means for containing a buffer and/or other diluent.

The kits of the present invention will also typically include a means for containing the vials in close confinement for commercial sale, such as, e.g., cardboard boxes or injection and/or blow-molded plastic containers into which the desired vials are retained.

Such kits may also include components that facilitate isolation of nucleic acids, such as filters, beads, or a magnetic stand. Such kits generally will comprise, in suitable means, distinct containers for each individual reagent or solution as well as for the targeting agent.

A kit will also include instructions for employing the kit components as well the use of any other reagent not included in the kit. Instructions may include variations that can be implemented.

D. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Optimized Polyadenylation of Bacterial mRNA

Seemingly straightforward and simple, the polyadenylation of complex RNA populations is actually a quite complicated reaction. For polyadenylating bacterial mRNAs, the inventors used purified poly(A) polymerase I (PAP I) enzyme of *E. coli*. PAP I or PAP adds AMP to 3' ends of RNA molecules using ATP as a donor. The efficiency of PAP has been found to vary with different substrate RNAs. RNAs with 3' end nucleotides that are paired, such as in a hairpin, are less efficiently polyadenylated (Feng and Cohen, 2000). The enzyme uses an ordered bi-bi kinetic mechanism and adds adenines distributively (Eun, 1996). Initiation and elongation occur at different rates, and the enzyme dissociates from the primer after every step.

The initial goal was to ensure that all mRNAs in a population of bacterial mRNA were poly(A) tailed, thereby ensuring that they will be templates for the 1$^{st}$ strand cDNA synthesis reaction—the first step in amplification. Using the standard reaction conditions for commercially available PAP enzymes and synthetic RNA transcripts, the inventor found that ~90-95% of a transcript could be tailed. It was also observed that with small mass amounts of RNA, such as those likely to be used for amplification (<100 ng), the tail lengths were extremely long—up to 9 kb in length. The inventors surmised that excessive tail-length could inhibit amplification reactions through several possible mechanisms: (1) reverse transcriptase may dissociate from the template during polymerization through extremely long homopolymeric A tracts; (2) dTTP may be effectively exhausted during 1$^{st}$ strand synthesis, slowing the reaction rate; (3) excess poly(A) may itself be detrimental to reaction kinetics; (4) UTP may become limiting during the in vitro transcription step; and/or (5) T7 polymerase may be hindered while incorporating long U tracts at the 5' ends of antisense RNAs (aRNAs).

To ensure more complete mRNA polyadenylation, and to limit tail lengths to a reasonable size (preferably <500 base pairs), new methodologies were developed.

To effectively monitor polyadenylation of mRNAs, several synthetic transcripts of various sizes (300-1500 nt) were individually evaluated, as even simple mixtures of a few transcripts were cumbersome to evaluate. Limiting tail lengths and ensuring that all of the transcript is tailed are intricately linked. Achieving one of the goals usually adversely affected the other. To optimize this procedure, the inventors altered numerous reaction constituents and parameters and tested novel reaction components and conditions.

The inventors first modified the reaction time (0-30 min), ATP amount (0-1 mM), and U of PAP (0-2 U) in the reaction. It was generally observed that longer reaction times, higher ATP concentration, and more PAP increased the percentage of the transcript that was tailed, but also increased the lengths of A tails. Under conditions where tail lengths were acceptably reduced, too much transcript was left untailed. The inventors also tested the chain-terminating nucleotides cordycepin and ddATP (0-50% exchange with ATP or with ATP held constant) and observed the same effect.

Tailing was also evaluated using thio-ATP, dATP, CTP, GTP, and UTP. GTP was not a substrate. CTP and UTP effectively limited tail lengths, leaving some untailed transcript. UTP would be a more useful substitute than CTP, because chemically synthesizing a poly(G) oligonucleotide (for subsequent priming of $1^{st}$ strand synthesis on C-tailed RNA) is problematic. None of these modifications appeared to be superior to using ATP.

Two reaction modifications: (1) adding a single stranded binding protein (e.g., T4 Gene32 protein); and (2) denaturing RNAs prior to their addition to the PAP reaction enabled the tailing of essentially 99-100% of a transcript. This was verified by analyzing reactions on RNA LabChips and by quantifying radiolabeled transcripts before and after tailing with a phosphorimager. Both methods indicated that <1% of the untailed transcript remains following the PAP reaction.

Limiting the size of A-tails appended to mRNAs was accomplished by drastically reducing the ATP concentration in the reaction to 25-50 µM and by reducing the reaction time to 5-15 min at 37° C. FIG. 1 shows an Agilent Bioanalyzer electropherogram depicting a synthetic GAPDH transcript before and after tailing. In this example, the untailed transcript is ~315 nucleotides, and the majority of the tailed transcript is ~570 nucleotides. However, some transcripts are tailed to greater lengths.

Example 2

Effect of $MnCl_2$ Concentration on Polyadenylation Reaction

This experiment was designed to test whether or not the addition of $MnCl_2$ has an effect on poly(A) tailing efficiency and tail length. The reaction utilized 100 ng of a synthetic in vitro transcribed RNA of 387 nucleotides as template. The reactions were performed as follows:

RNA template (100 ng) and $H_2O$ to a final volume of 10 µl were combined in a 0.5 ml tube. The RNA solution was heat denatured at 70° C. for 10 minutes and then quenched on ice for 3 minutes. The other reactants were then added as a 15 µl cocktail containing: 5 µl 5× Polyadenylation buffer, 1.25 µl 1 mM ATP, 1 µl Ribonuclease inhibitor (40 U/µl), 1 µl E. coli Poly(A) Polymerase (2 U/µl) and 4.25 µl $H_2O$. Depending on the reaction (with $MnCl_2$ or without $MnCl_2$) either 2.5 µl 25 mM $MnCl_2$ or 2.5 µl $H_2O$ was also added. The reactions were allowed to incubate at 37° C. for various time points. At the end of this incubation 2 µl of 0.5 M EDTA was added to stop the reactions. The negative control had EDTA added prior to the reactant cocktail, thus preventing tailing. Finally the reactions were purified with a variation of Ambion's MegaClear glass-fiber based RNA purification kit.

Figure 2:
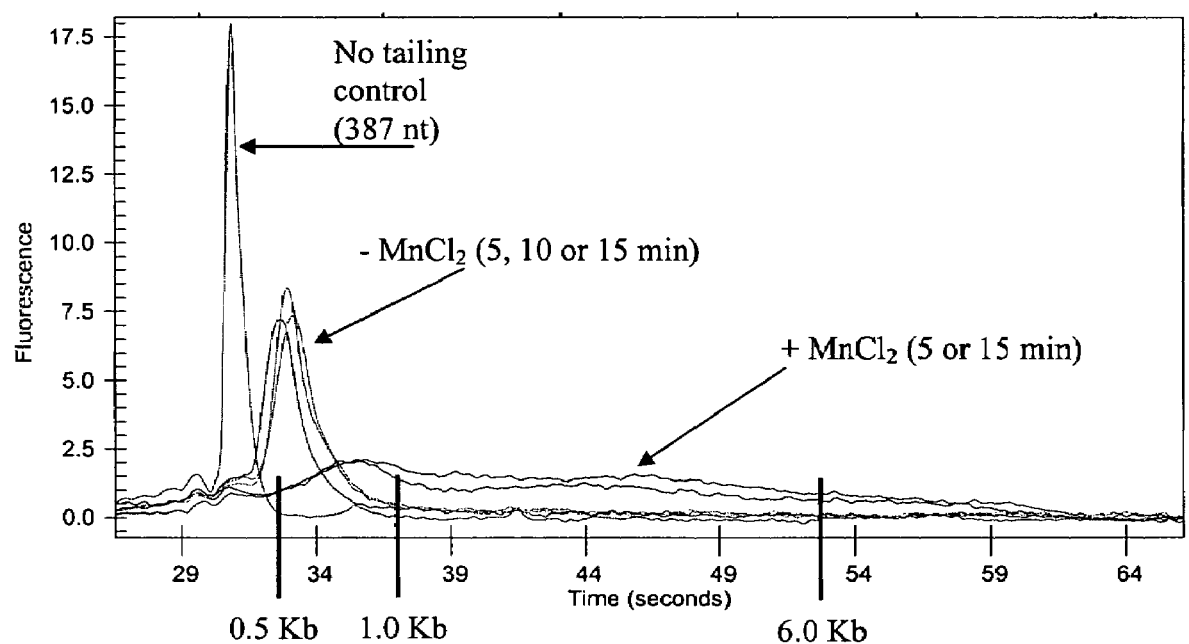
FIG. 2.

Shown in FIG. 2 is an Agilent Bioanalyzer electropherograms depicting the extent of polyadenylation for various reaction conditions. All of the polyadenylation reaction was run on the Bioanalyzer. As can be seen in FIG. 2, $MnCl_2$ had a dramatic effect on tail length. When the reaction was performed with $MnCl_2$ [2.5 mM] tail length extended from ~0.5 Kb to beyond 6 Kb. When $MnCl_2$ was not added to the reaction, tail length was reduced dramatically, to a median size of ~150 nt. While incubation time had some effect, it was small relative to the MnCl2 effect.

Example 3

Bacterial RNA Amplification

In this experiment total E. coli RNA was polyadenylated and amplified. Two RNA preparations were used (lot # PR043921 and the same RNA after purification over a glass fiber filter column) for amplification and two in vitro transcription (IVT) incubation times were compared (6 hours and 14 hours).

Total RNA template (10 ng or 100 ng) and $H_2O$ to a final volume of 5 µl were combined in a 0.5 ml tube. The RNA solution was heat denatured at 70° C. for 10 minutes and then quenched on ice for at 3 minutes. The other reactants were then added as a 5 µl cocktail containing: 1× Polyadenylation buffer (50 mM Tris-HCl pH 8.3, 75 mM KCl, 3 mM $MgCl_2$ and 10 mM DTT), 50 µM ATP, 40 Units Ribonuclease inhibitor Protein, 2 Units E. coli Poly(A) Polymerase. The reaction was incubated for 15 minutes at 37° C. and placed on ice until the amplification step.

Ambion's MessageAmp II RNA amplification kit was used to amplify the polyadenylated bacterial RNA according to the manufacturer's instructions, with only minor changes. An anchored T7(dT)VN primer was used, and there was no denaturation step of the RNA/primer prior to reverse transcription. In vitro transcription was performed for either 6 or 14 hours. Table 1 below shows the aRNA yields and mean and the coefficient of variation expressed in percent (% CV) for triplicate reactions.

TABLE 1

| Yield (µg) | Triplicate Mean | % CV | Description |
| --- | --- | --- | --- |
| 137.5245 | 130.0 | 5.38 | 100 ng total RNA-organic isolation, 14 hour IVT |
| 123.726 | | | |
| 128.604 | | | |
| 80.0175 | 78.0 | 2.96 | 10 ng total RNA-organic isolation, 14 hour IVT |
| 75.465 | | | |
| 78.387 | | | |
| 206.907 | 198.5 | 4.24 | 100 ng total RNA-glass fiber purified, 14 hour IVT |
| 190.065 | | | |
| 198.51 | | | |
| 68.6355 | 66.4 | 11.18 | 10 ng total RNA-glass fiber purified, 14 hour IVT |
| 72.537 | | | |
| 58.1715 | | | |
| 61.9035 | 56.9 | 9.22 | 100 ng total RNA-organic isolation, 6 hour IVT |
| 57.2445 | | | |
| 51.444 | | | |
| 33.3465 | 33.6 | 8.74 | 10 ng total RNA-organic isolation, 6 hour IVT |
| 36.6825 | | | |
| 30.8265 | | | |
| 108.4545 | 111.1 | 2.57 | 100 ng total RNA-glass fiber purified, 6 hour IVT |
| 110.667 | | | |
| 114.114 | | | |
| 22.0875 | 31.3 | 28.63 | 10 ng total RNA-glass fiber purified, 6 hour IVT |
| 31.8465 | | | |
| 39.987 | | | |

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,545,522
U.S. Pat. No. 5,716,785
U.S. Pat. No. 5,891,636
U.S. Pat. No. 6,204,375
U.S. Pat. No. 6,528,641
U.S. patent application Ser. No. 09/854,412
U.S. patent application Ser. No. 10/667,126
U.S. patent application Ser. No. 10/460,775
U.S. patent application Ser. No. 10/360,772
U.S. patent application Ser. No. 10/355,820
U.S. patent application Ser. No. 10/298,480
U.S. Patent App. 60/490,325
U.S. Patent Appl. 60/575,743
U.S. patent application Ser. No. 10/029,397
Absire and Neidhardt, *J. Bacteriol.*, 175:3734-3743, 1993.
Abu Kwaik and Pederson, *Mol. Microbiol.*, 3:543-546, 1996.
Abu Kwaik, *Infect. Immun.*, 66:203-212, 1998.
Amara and Vijaya, *Nucleic Acids Res.*, 25(17):3465-3470, 1997.
Arfin et al., *J. Biol. Chem.*, 275:29672-29684, 2000.
Aviv and Leder, *Proc. Natl. Acad. Sci. USA*, 69(6):1408-1412, 1972.
Boschiroli et al., *Proc. Natl. Acad. Sci. USA*, 99:1544-1549, 2002.
Cao and Sarkar, *Biochem. Biophys. Res. Commun.*, 239(1): 46-50, 1997.
Conway and Schoolnik, *Mol. Microbiol.*; 47:879-889, 2003.
DeRisi et al., *Nature Genetics*, 14:457-460, 1996.
Dietrich et al., *J. Bacteriol.*, 185:155-164, 2003.
Engel and Davidson, *Biochemistry*, 17(18):3883-3888, 1978.
Eriksson et al., *Mol. Microbiol.*, 47:103-118, 2003.
Eun, In: *Enzymology Primer for recombinant DNA Technology*, Academic Press, NY, 555-565, 1996.
Feng and Cohen, *Proc. Natl. Acad. Sci. USA*, 97:6415-6420, 2000.
Fodor et al., *Science*, 251:767-773 (1991).
Graham and Clark-Curtiss, *Proc. Natl. Acad. Sci. USA*, 96:11554-11559, 1999.
Grifantini et al., *Nat. Biotechnol.*, 20:914-921, 2002.
Hensel et al., *Science*, 269:400-403, 1995.
Khil and Camerini-Otero, *Mol. Microbiol.*, 44:89-105, 2002.
Kricka et al., *Clin. Chem.*, 38(12):2558-2560, 1992.
Lockhart et al., *Nat. Biotechnol.*, 14(13):1675-1680, 1996.
Mahan et al., *Science*, 259:686-688, 1993.
Maskos and Southern, *Nucleic Acids Res.*, 20(7):1679-1684, 1992.
Mohanty and Kushner, *Mol. Microbiol.*, 34(5):1109-1119, 1999.
Mohanty and Kushner, *Mol. Microbiol.*, 36(4):982-994, 2000.
Monahan et al., *Microbiology*, 147:459-471, 2001.
Pietu et al., *Genome Res.*, 6(6):492-503, 1996.
Plum and Clark-Curtiss, *Infet. Immun.*, 62:476-483, 1994.
Read and Norbury, *J. Cell Biochem.*, 87(3):258-265, 2002.
Sambrook et al., In: *Molecular cloning*, Cold Spring Harbor Laboratory Press, Cold Spring Harbor, N.Y., 1989.
Sambrook et al., In: *Molecular cloning*, Cold Spring Harbor Laboratory Press, Cold Spring Harbor, N.Y., 2001.
Sassetti and Rubin, *Curr. Opin. Microbiol.*, 5:27-32, 2002.
Schena et al., *Proc. Natl. Acad. Sci. USA*, 93:10614-10619, 1996.
Schena, et al., *Science*, 270:467-470, 1995.
Schoolnik, *Curr. Opin. Microbiol.*, 5:20-26, 2002.
Scott-Craig et al., *Mol. Gen. Genet.*, 228:356-360, 1991.
Shalon et al., *Genome Res.*, 6(7):639-645, 1996.
Staudinger et al., *J. Clin. Invest.*, 110:1151-1163, 2002.
Taha et al., *Mol. Microbiol.*, 6:1153-1163, 1998.
Triccas et al., *Microbiology*, 145:2923-2930, 1999.
Valdiva and Falkow, *Science*, 277:2007-2011, 1997.
Wendisch et al., *Anal Biochem.*, 290(2):205-213, 2001.
Yehudai-Resheff et al., *Nucleic Acids Res.*, 28(5):1139-1144, 2000.
Zhao et al., *Gene*, 166:207-213, 1995.

What is claimed is:

1. A method for amplifying a targeted RNA in a sample comprising:
   (a) altering the secondary structure of the targeted RNA by denaturing the targeted RNA or contacting the targeted RNA with a single-stranded binding protein;
   (b) incubating the targeted RNA in the presence of poly (A) polymerase I of *E. coli* and a nucleotide under conditions that allow tailing of the targeted RNA wherein said conditions include a buffer lacking $Mn^{2+}$ and, for RNA amounts in the range of 1-100 ng, the nucleotide concentration is 5-350 µM;
   (c) hybridizing the targeted RNA with a promoter-oligo-dN primer complementary to the tail of the targeted RNA;
   (d) extending the promoter-oligo-dN primer using a reverse transcriptase to form a first strand complementary to the targeted RNA;
   (e) synthesizing a second strand complementary to the first strand; and
   (f) transcribing copies of RNA initiated from the promoter-oligo-dN primer using an RNA polymerase, wherein the RNA is complementary to the second strand.

2. The method of claim 1, wherein altering the secondary structure of the targeted RNA comprises denaturing the targeted RNA.

3. The method of claim 2, wherein denaturing the targeted RNA is further defined as heating the targeted RNA for at least 10 minutes at a temperature of at least about 70° C.

4. The method of claim 1, wherein altering the secondary structure of the targeted RNA comprises contacting the targeted RNA with a single-stranded binding protein a single strand binding protein.

5. The method of claim 1, wherein the sample comprises a mixture of eukaryotic RNA and prokaryotic RNA.

6. The method of claim 1, wherein the targeted RNA is a non-polyadenylated mRNA; an miRNA, an siRNA, or a synthetic RNA.

7. The method of claim 6, wherein the non-polyadenylated mRNA is a bacterial mRNA.

8. The method of claim 6, wherein the non-polyadenylated mRNA is a degraded mRNA.

9. The method of claim 1, wherein the sample is further defined as obtained from a cell, cell culture, a body fluid, a tissue, or an organ.

10. The method of claim 9, wherein the tissue is a fixed tissue or a frozen tissue.

11. The method of claim 1, wherein the sample is an environmental sample.

12. The method of claim 11, wherein the environmental sample is a soil sample, a water sample, or an air sample.

13. The method of claim 1, further comprising depleting polyadenylated mRNA from the sample prior to tailing the targeted RNA.

14. The method of claim 1, further comprising depleting rRNA from the sample.

15. The method of claim 1, wherein at least 95% of the targeted RNA is tailed.

16. The method of claim 1, wherein the tail added on to a majority of the targeted RNA molecules comprises about 20 nucleotides to about 500 nucleotides.

17. The method of claim 1 further comprising using the amplified targeted RNA for expression analysis.

18. The method of claim 4, wherein the single strand binding protein is T4 Gene 32 protein.

19. The method of claim 1, wherein the promoter-oligo-dN primer is a T7-oligo-dT primer or an SP6-oligo-dT primer.

20. The method of claim 1, wherein the RNA polymerase is a T7 RNA polymerase, SP6 RNA polymerase, or T3 RNA polymerase.

21. The method of claim 1, wherein the reverse transcriptase is an MMLV reverse transcriptase or an avian myeloblastosis virus reverse transcriptase.

22. The method of claim 1, wherein the reverse transcriptase is mutant reverse transcriptase having reduced or absent RNase activity.

23. The method of claim 1, wherein the reverse transcriptase is mutant reverse transcriptase engineered to have high thermal stability tip to 70° C.

24. A method for tailing a targeted RNA in a sample comprising:
   (a) denaturing the targeted RNA; and
   (b) incubating the targeted RNA in the presence of poly (A) polymerase I of *E. coli* and a nucleotide under conditions that allow tailing of the targeted RNA wherein said conditions include a buffer lacking $Mn^{2+}$ and, for RNA amounts in the range of 1-100 ng, the nucleotide concentration is 5-350 µM.

* * * * *

UNITED STATES PATENT AND TRADEMARK OFFICE
CERTIFICATE OF CORRECTION

PATENT NO. : 7,361,465 B2
APPLICATION NO. : 10/935534
DATED : April 22, 2008
INVENTOR(S) : Murphy et al.

It is certified that error appears in the above-identified patent and that said Letters Patent is hereby corrected as shown below:

Claim 1, Column 27, line 6, delete "single-stranded" and insert -- single strand -- therefore.

Claim 4, Column 27, line 33, delete "a single-stranded binding protein".

Signed and Sealed this

Nineteenth Day of August, 2008

JON W. DUDAS
*Director of the United States Patent and Trademark Office*

SEQUENCE LISTING

<160> NUMBER OF SEQ ID NOS: 1

<210> SEQ ID NO 1
<211> LENGTH: 53
<212> TYPE: DNA
<213> ORGANISM: Artificial Sequence
<220> FEATURE:
<223> OTHER INFORMATION: Description of Artificial Sequence: Synthetic Primer

<400> SEQUENCE: 1
ggtaatacga ctcactatag ggagaagagt ttttttttt tttttttttt ttt          53